(12) United States Patent
Pelissier

(10) Patent No.: US 6,669,735 B1
(45) Date of Patent: Dec. 30, 2003

(54) PROSTHESIS FOR SURGICAL TREATMENT OF HERNIA

(75) Inventor: Edouard P. Pelissier, Devecey (FR)

(73) Assignee: Davol, Inc., Cranston, RI (US)

( * ) Notice: Subject to any disclaimer, the term of this patent is extended or adjusted under 35 U.S.C. 154(b) by 0 days.

(21) Appl. No.: 09/762,010

(22) PCT Filed: Jul. 13, 1998

(86) PCT No.: PCT/FR98/01710

§ 371 (c)(1),
(2), (4) Date: Jun. 22, 2001

(87) PCT Pub. No.: WO00/07520

PCT Pub. Date: Feb. 17, 2000

(51) Int. Cl.[7] ................................................. A61F 2/02
(52) U.S. Cl. .................. 623/23.74; 623/23; 623/75; 606/151
(58) Field of Search ...................... 623/23.64, 23.72, 623/23.74, 23.76, 23.23, 23.48, 23.75; 602/44, 76, 75, 58; 606/151, 154

(56) References Cited

U.S. PATENT DOCUMENTS

| | | | | |
|---|---|---|---|---|
| 5,116,357 A | * | 5/1992 | Eberbach | 602/76 |
| 5,254,133 A | * | 10/1993 | Seid | 128/899 |
| 5,356,432 A | * | 10/1994 | Rutkow et al. | 600/37 |
| 5,368,602 A | * | 11/1994 | de la Torre | 602/44 |
| 5,397,331 A | * | 3/1995 | Himpens et al. | 128/899 |
| 5,634,931 A | * | 6/1997 | Kugel | 606/1 |
| 5,766,246 A | * | 6/1998 | Mulhauser et al. | 606/151 |
| 5,824,082 A | * | 10/1998 | Brown | 623/11.11 |

* cited by examiner

Primary Examiner—Nicholas D. Lucchesi
Assistant Examiner—Quang D Thanh
(74) Attorney, Agent, or Firm—Wolf, Greenfield & Sacks, P.C.

(57) ABSTRACT

A prosthesis is provided for the surgical treatment of hernias. The prosthesis includes two parts, that is, a synthetic non-resorbent mesh and a ring fixed at the peripheral edge of the synthetic mesh. The ring, which is made of a resorbent material, is of a flexibility that permits it to bend, then resume its initial shape to give the mesh a memory of its initial shape. The ring has an interruption intended to be positioned over the femoral veins.

37 Claims, 2 Drawing Sheets

PROSTHESIS FOR SURGICAL TREATMENT OF HERNIA

BACKGROUND OF THE INVENTION

The subject of this invention is a prosthesis for the surgical treatment of hernias.

A hernia is a defect in the abdominal wall into which the peritoneum and the intra-abdominal viscera thrust themselves. It is most often located at the groin and the navel. There are also hernias called ruptures located at incisions made during a surgical operation on the abdomen.

Surgical repair of hernias has two goals, first, to assure the solidity of the wall definitively so there will be no recurrence and, second, to do it with as little inconvenience as possible, particularly with little pain in order to permit rapid resumption of activity.

We note that where inguinal hernia in men is concerned, the repair work is more complicated than the simple closing of an orifice because the inguinal cord which contains the testicle ducts and the vas deferens must be preserved.

The surgical treatment of hernias may be carried out by sutures pulling together the edges of the hernial orifice or by putting in place a prosthesis in synthetic mesh to seal the orifice without bringing together the edges. With a prosthesis, the absence of tension alleviates the pain and reduces the risk of recurrence.

There are several types of prostheses, all made of a supple mesh of synthetic material, notably of material like dacron, polyethylene, PTFE, etc.

Existing prostheses are offered in several shapes. The most common have the shape of a rectangle or a square of supple tissue that can be applied as is or cut as desired.

Some are precut, usually in oval shape adapted to the area of weakness of the inguinal hernia with a slit for passage of the inguinal cord. Others are molded with a certain convexity adapted to the shape of the abdominal wall.

There is, also, a prosthesis called "plug" which consists of a sort of conically shaped cork, intended to be introduced into the hernial orifice to obstruct it.

The setting in place of prostheses may be done in various ways, in particular by the inguinal, retroperitoneal route or by laparoscopy.

The retroperitoneal method or Stoppa procedure necessitates making a large median abdominal incision in order to access the retroperitoneal space and the bottom surface of the muscular system. Admittedly this technique permits the expansive spreading out of a supple prosthesis on the bottom surface of the muscular wall, so that abdominal pressure holds the prosthesis against the wall around the hernial orifice, giving it great solidity.

However, you will see that the retroperitoneal method has the disadvantages of requiring a debilitating and painful incision and, moreover, cannot be done under local anesthetic.

Laparascopy permits placing the prosthesis in the retroperitorieal space, while avoiding the making of a large incision. However, this technique is proving difficult to perform and requires great expertise on the part of the surgeon, not to mention that it cannot be done under local anesthetic. In addition, this technique is likely to expose the patient to complications, some of which may be serious.

The inguinal route consists of cutting directly into the inguinal region and then, after dissection of the anatomic elements, putting the prosthesis in place, either in the retroperitoneal space (Rives procedure), or on the surface wall of the musculo-aponeurotic system (Lichtenstein procedure).

This technique has the advantage of being simple, easily reproduced and doable under local anesthesia. However, we see that with this technique it is particularly difficult to set a prosthesis in place in the retroperitoneal space, guaranteeing optimal solidity. In fact, due to the narrowness of the passage, spreading out prostheses which are at present supple, proves difficult and they have a tendency to wrinkle. The absence of perfect spreading on the bottom surface of the muscular wall brings a risk of engagement of the peritoneal sac and increases the possibilities of a relapse.

To make up for these disadvantages, various devices facilitating the setting in place and spreading out of prostheses in the retroperitoneal space have been proposed. So, through documents EP-0.557.964 and WO-92.06639, we know of apparatus consisting of a device that is intended to make deployment of the prosthesis in the retroperitoneal space easier. In fact, these pieces of apparatus consist of a tubular device completed by a sheath and a button permitting introduction of the prosthesis through a laparoscopy trocar and obtaining its deployment through that trocar.

We note that these devices are, in fact, mainly intended for putting in place prostheses by the laparoscopic method, but are not in any way intended to be used for the inguinal method in traditional surgery.

We also know from document WO-96.09795 of a prosthesis constituted by two superimposed layers of mesh surrounded by a peripheral frame intended to give it sufficient rigidity to facilitate setting it in place and spreading it out in the retroperitoneal space.

You will notice that this prosthesis is made up of several thicknesses of mesh in a non-resorbent material of a synthetic type and that the multiplication of these thicknesses leads to an increase of risks of intolerance by the organism, notably in case of infection.

The framework, also, is made up of a non-resorbent material and is presented in the form of a relatively thick and rigid ring with no interruption. This ring then rests against the femoral veins which, over time, may traumatize them and bring about complications. Moreover, the circumference of this prosthesis has rough patches due to cutting the free edge and intended to facilitate anchoring said prosthesis in the tissues of patients. These rough patches are also likely to traumatize the tissues, particularly the femoral veins and the vas deferens. In addition, this flat, rigid prosthesis does not fit properly the convex shape of the visceral sac and abdominal wall.

Finally, through document WO-97.23310, we know about a prosthesis composed of a supple sheet associated with a self-opening structural device intended to facilitate the deployment of the prosthesis in the retroperitoneal space when it is set in place through the inguinal orifice or by a laparoscopy trocar. This device can take on a curved shape, facilitating, solely, the expansion and setting in place of one of the ends of the prosthesis, but not resolving in any way the difficulties in spreading out the other end. This device can, also, take the shape of a ring whose circumference necessarily rests on the femoral veins with the risks of traumatism to them mentioned above. Moreover, the non-resorbent nature of the material used for the creation of the ring of this prosthesis once again exposes the patient to the risk of intolerance. Finally, the flat shape of this prosthesis is incapable of adapting properly to the convexity of the peritoneal sac and the viscera it contains.

SUMMARY OF THE INVENTION

The aim of this invention is to offer a prosthesis for the surgical treatment of hernias, implant able by the inguinal route under local or loco-regional anesthesia and that remedies the previously mentioned disadvantages.

The prosthesis that is the subject of this invention is characterized essentially by the fact that it is composed of two parts, that is, a synthetic non-resorbent mesh and a ring fixed to the peripheral edge of said synthetic mesh, said ring being made of a flexible resorbent material, permitting it to bend out of shape and then resume its initial form; and by the fact that said ring offers an interruption intended to be positioned over the femoral veins.

According to an additional characteristic of the device of the invention, the association of the said mesh and the said ring is realized in such a way that said mesh inside the said ring maintains a certain laxity, permitting it to take on a convex shape. This permits a perfect fit of the mesh to the convexity of the peritoneal sac and to the concavity of the bottom abdominal wall.

According to another additional characteristic of the prosthesis of the invention, at least one divider positioned diametrically is fastened by its ends to the ring and said divider, made of the same material as the said ring, is curved in shape and holds the mesh in a convex form.

According to another additional characteristic of the prosthesis of the invention, each of the end parts of the ring, on both sides of the interruption, presents, near the extreme edge, a zone of lesser resistance, permitting the said interruption to expand. This permits easy cutting of the ring.

According to another additional characteristic of the prosthesis of the invention, the mesh has, at each of the edge ends of the ring, a radial slit, creating a tongue intended to be applied over the femoral veins. This avoids, at the free edge of the prosthesis, any pressure whatsoever being applied on the said femoral veins.

According to a particular method of creation of the prosthesis of the invention, the latter is round in shape and comprised concentrically in the peripheral ring of an empty ring inside the mesh, linked to the said peripheral ring by means of spokes and presenting an interruption with regard to the interruption of said peripheral ring, the edge ends of the rings being linked in pairs by two of said spokes between which there is no mesh, while a cord is threaded peripherally close to the said peripheral ring; said cord permits, by traction on both of its ends, shaping the prosthesis into a frustum, presenting a space laterally.

According to an additional characteristic of the prosthesis of the invention, the ring or rings, together with the possible dividers or spokes, are made up of fine strips of round or flattened sections.

According to an additional characteristic of the prosthesis of the invention, the ring or rings, together with the possible dividers or spokes, are made of a resorbent material, notably like polyglycolic acid.

The advantages and the characteristics of the device of the invention will emerge more clearly from the description which follows and which refers to the annexed diagram, which shows several non-limiting methods of production.

DETAILED DESCRIPTION OF THE INVENTION

Figure 1:
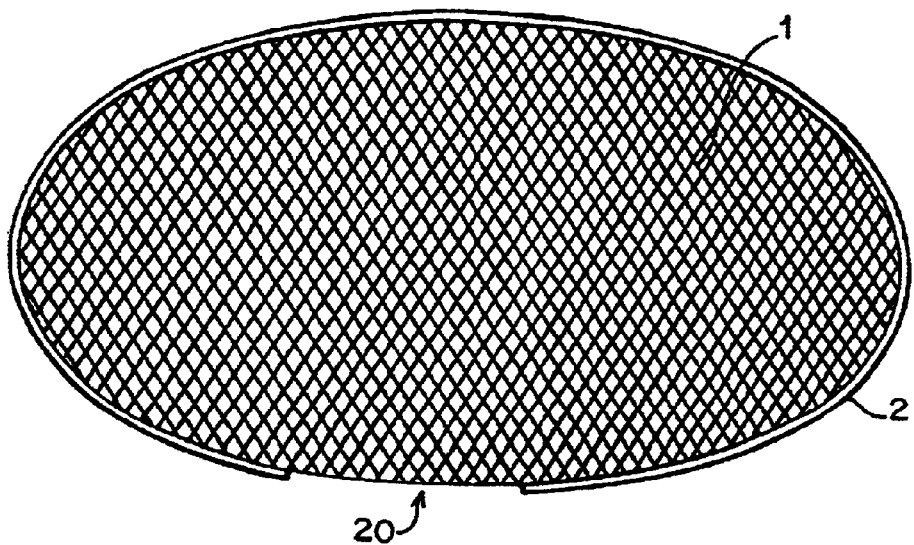
FIG. 1 shows a surface view of a first method of production of the prosthesis according to the invention.
Figure 2:
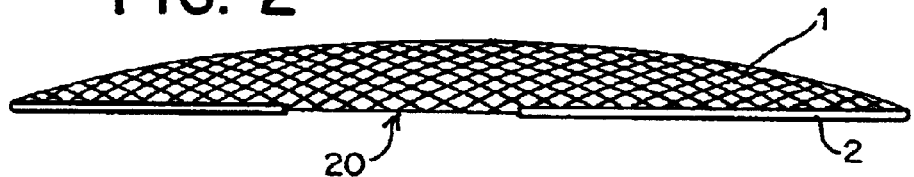
FIG. 2 shows a profile view of the same prosthesis.

With reference to FIGS. 1 and 2, we can see that according to a first method of production, the prosthesis according to the invention consists of a mesh 1 in oval shape bordered by a ring 2. The mesh 1 is fastened to the ring 2 in such a way as to not be under tension, that is, conserving a certain laxity that permits it to take on a convex shape as is visible in FIG. 2.

The mesh 1 is made of a synthetic non-resorbent material of the polypropylene type, while the ring 2 is made of a resorbent material of polyglycolic acid type.

The ring is intended to recall its shape to the mesh when it is set in place by the inguinal route. It is sufficiently supple to be bendable without breaking at the moment of its introduction and rigid enough to resume its initial shape and to restore tension to the mesh 1 in the retroperitoneal space.

The mesh 1 is thus completely spread out and has no folds, because its original convex shape allows it to fit into the visceral sac and the concave shape of the bottom surface of the abdominal wall. In connection with this, we note that, according to a particular method of production, the convexity of the mesh 1 may be given to it when it is manufactured, specifically by molding.

The prosthesis may be of several shapes, oval, round to go on top of the roughly rounded subsistence discharges in the case of an umbilical hernia or a rupture, or pear-shaped, that is, more or less oval with one narrower end. They can also have varying dimensions in order to be applicable to different types of hernias or ruptures.

While on this subject, and in the case of an oval-shaped prosthesis, the dimensions of the latter are 8 to 14 centimeters, preferably 12 centimeters for the large axis and 6 to 10 centimeters, preferably 8 centimeters for the small axis.

We can also see in FIG. 1 that the ring 2 shows an interruption 20 which is intended to be positioned at the femoral veins so as not to traumatize them. In this confirmation, the surgeon can slit the mesh 1 with scissors over several centimeters to create a tongue which is applied, without tension, over the femoral veins.

Figure 3:
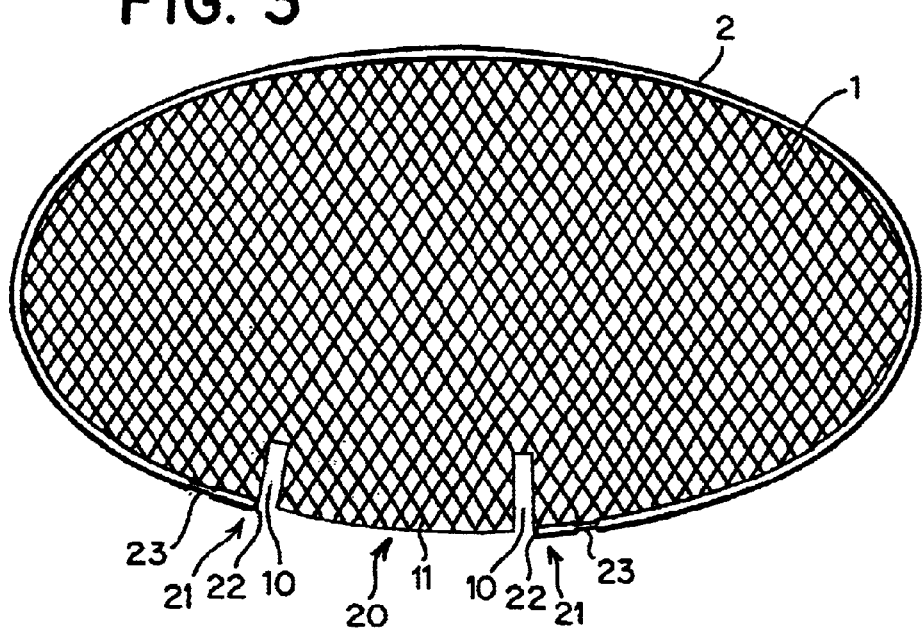
FIG. 3 shows a surface view of a variation of the same prosthesis.

Referring now to FIG. 3, we can see that in one variation each of the end parts 21 of the ring 2 at the interruption 20, have, close to the end 22 of the ring 2, an area 23 of less resistance permitting the ring 2 to be broken so that the interruption 20 may be enlarged if that is necessary.

On the other hand, the mesh 1 has two more or less radial slits 10 one at each of the ends 22 of the ring 2, permitting the creation of a tongue 11 to be applied over the femoral veins to avoid their traumatization by the free edge of the mesh 1 which, without the slits 10, would be under tension.

We note that the presence of the slits 10 can be independent of the presence of the areas of less resistance 23.

Figure 4:
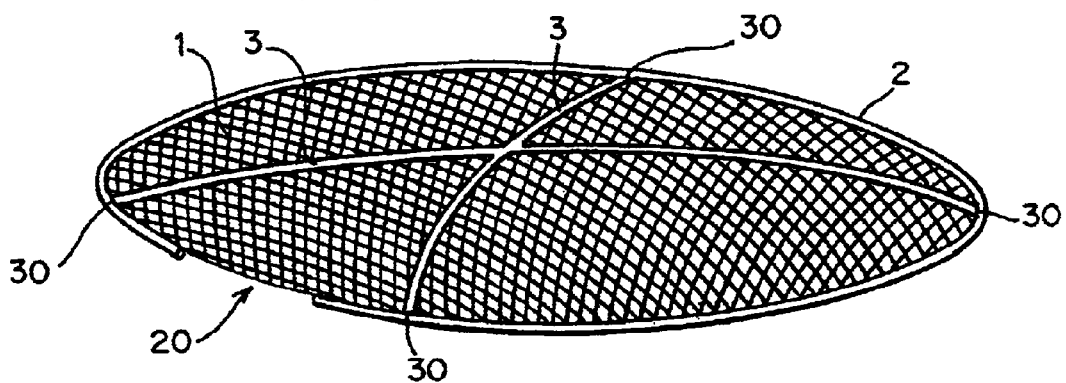
FIG. 4 shows an angle view of another variation of the same prosthesis.

If we look now at FIG. 4, we can see that according to one variation of the prosthesis according to the invention, the ring 2 is connected to two diametrical dividers 3 crossing over each other in an approximate right angle and made of the same resorbent material as the ring 2.

The dividers 3 are fastened by their ends 30 to the ring 2 and their lengths are chosen so that they can take on a curved shape, permitting the convexity of the mesh 1 to be maintained.

In this variation, the dividers 3 are preferably two in number, but it is of course possible that a prosthesis according to the invention may consist of either a single divider or more than two dividers. In this confirmation, the position of the interruption 20 of the ring 2 must be different depending on whether it is a matter of the right side or the left side. If we refer now to FIG. 5, we can see that according to a second method of production, the prosthesis is round in form, the ring 2 is doubled by an internal concentric ring 4, with no mesh inside it and linked to the ring 2 by means of spokes 5.

Concerning this, we see that such a prosthesis has dimensions on the order of 4 to 7 centimeters, preferably 5 centimeters, for the external diameter of the ring 2 while the internal ring 4 has a diameter of 1 to 2 centimeters.

With regard to the interruption 20 of the ring 2, the ring 4 has an interruption 40, the end edges 22 of the ring 2 being linked to the free edges 41 of the ring 4 by two spokes 5 linking the interruptions 20 and 40 defining a space 50.

Figure 5:
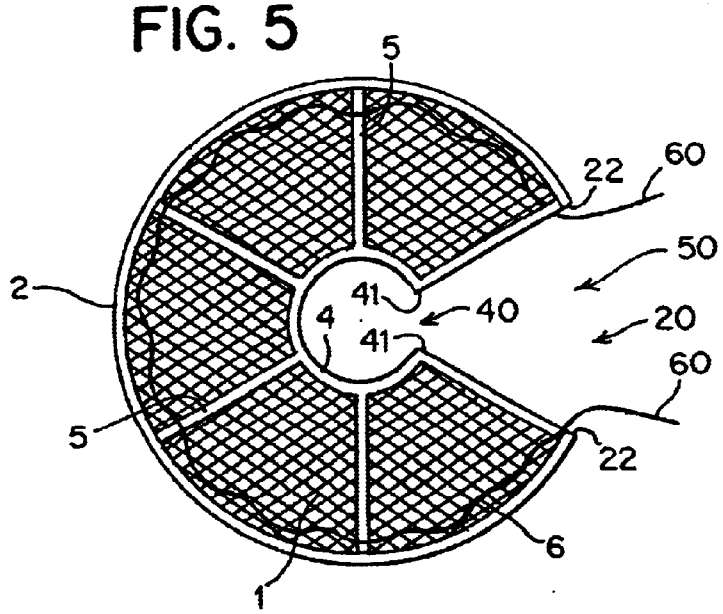
FIG. 5 shows a surface view of a second method of production of the prosthesis according to the invention.

According to a first method of production represented by FIG. 5, between the spokes 5 defining space 50, there is no mesh. However, and according to another method of creation shown in FIG. 6, at least one of the spokes 5 defining said space 50 is provided with a tongue 51 of mesh, notably of a mobile type. Such a tongue extends to the interior of said space 50 and is intended to be placed over the femoral veins.

Figure 6:
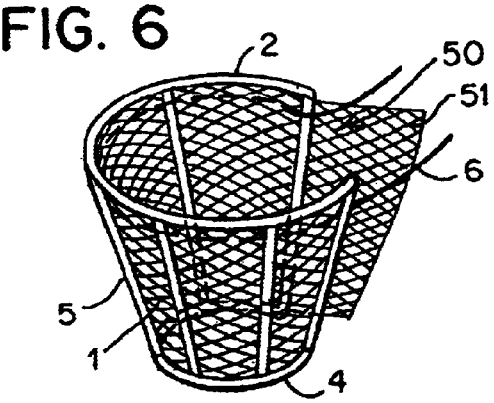
FIG. 6 shows an angle view of the same prosthesis in its configuration for setting in place.

A cord 6, preferably of a resorbent material, is threaded peripherally through the mesh 1 close to the ring 2 and this cord, through a traction on its two ends 60 which emerge at the interruption 20, permits forming the prosthesis into a frustum as is shown in FIG. 6.

The prosthesis thus shaped constitutes an umbrella prosthesis intended for the treatment of indirect inguinal hernias.

In this configuration, the prosthesis may be set in place by being introduced into the inguinal orifice, small diameter first and the space 50 defined by the two spokes 5 linking the interruptions 20 and 40 and being destined for passage of the inguinal cord.

After introduction of the prosthesis, the cord 6 is removed, permitting the prosthesis to spread out like an umbrella, due to the elastic effect of the two rings 2 and 4 and the spokes 5.

Now it is appropriate to describe briefly the technique for setting in place such a prosthesis.

So, it is advisable, after local or loco-regional anesthesia, to make an inguinal incision and to open the inguinal canal by making an incision in the aponeurosis. Next a series of incisions and/or dissections is made adapted to the type, direct or indirect, of the hernia treated.

In the case of setting in place a prosthesis like that illustrated in FIGS. 1 to 4, the dissection of the retroperitoneal space is then assured before introducing said prosthesis. This latter is flattened transversely between the fingers of one hand and is slid into the slit by its first end. The prosthesis, if necessary, is then subjected to a slight bending to assure introduction of the second end. It is then spread out in the retroperitoneal space, the ring 2 permitting it to resume its initial form. The position of the prosthesis is adjusted so that the femoral veins are facing the interruption 20 of the ring 2, the mesh 1 being possibly slit, specifically with scissors in order not to exert pressure on the said femoral veins. The prosthesis can then be anchored, specifically by suture, before closing the incisions.

If it is a matter of setting in place a prosthesis like the one illustrated in FIGS. 5 and 6, after opening the inguinal canal, a dissection is made in the preperitoneal space so as to create a small receptacle destined to receive the prosthesis. The latter is, then formed in a frustum, placed around the free edge of the inguinal canal and introduced into the inguinal orifice, small diameter first. The cord 6 is then severed, permitting the prosthesis to spread out, possibly aided digitally, before assuring the position of the latter and, if necessary, its fixation before closing the incisions.

The result of this is that whatever the method of creation of the prosthesis according to the invention, its placement is easy and quick and it can be done under local or loco-regional anesthesia.

The mesh 1 always remains deployed and is applied perfectly without folds on the bottom surface of the muscolo-aponeurosis.

What is claimed is:

1. A prosthesis for the surgical treatment of a hernia, comprising:
a synthetic, non-absorbable patch having a peripheral edge and at least one semi-rigid element on the peripheral edge, the semi-rigid element including a hoop attached to the peripheral edge of the patch, the hoop extending continuously about the peripheral edge and substantially surrounding the patch to urge the patch into a spread out configuration that is constructed and arranged to overlie the hernia, the hoop having an interruption adapted to be positioned opposite the femoral vessels, wherein the hoop is made of an absorbable material and has a flexibility that allows the hoop to deform from an initial shape and then go back to the initial shape to return the patch to the spread out configuration.

2. The prosthesis according to claim 1, wherein the patch and the hoop are configured so that the patch maintains a certain slack within the hoop allowing the patch to take a convex shape.

3. The prosthesis according to claim 1, further comprising at least one divider having two ends, the divider being positioned diametrically with the ends joined to the hoop, the divider being made of the same material as the hoop and having a curved shape to keep the patch in a convex shape.

4. The prosthesis according to claim 1, wherein each end part of the hoop, on either side of the interruption, has near an extreme edge thereof a zone of less resistance that is adapted to enlarge the interruption.

5. The prosthesis according to claim 1, wherein the patch has a radial slot at each extreme edge of end parts of the hoop on either side of the interruption that form a tab designed to be applied to the femoral vessels.

6. The prosthesis according to claim 1, wherein the prosthesis is round in shape and has, concentric to the peripheral hoop, a second hoop that is connected to the peripheral hoop by spokes, the second hoop having a second interruption facing the interruption of the peripheral hoop, extreme edges of the peripheral hoop being connected to extreme edges of the second hoop by two of the spokes, there being no patch between the two spokes and within the second hoop, the prosthesis further comprising a thread that is threaded peripherally near the peripheral hoop, the thread being adapted to shape the prosthesis into a truncated cone with a lateral space by traction on two ends of the thread.

7. The prosthesis according to claim 1, wherein the prosthesis is round in shape and has, concentric to the peripheral hoop, a second hoop that is connected to the peripheral hoop by spokes, the second hoop having a second interruption opposite the interruption in the peripheral hoop, extreme edges of the peripheral hoop being connected to extreme edges of the second hoop by two of the spokes, at least one of the spokes being provided with a patch tab extending into a space delimited by the two spokes, the prosthesis further comprising a thread that is threaded peripherally near the peripheral hoop, the thread being adapted to form the prosthesis into a truncated cone with a lateral space by traction on two ends of the thread.

8. The prosthesis according to claim 3, wherein the hoop and the dividers are composed of fine rods that are round or flat in cross section.

9. The prosthesis according to claim 3, wherein the hoop and the dividers are made of an absorbable material comprising polyglycolic acid.

10. A prosthesis for repairing a hernia, the prosthesis comprising:
a flexible patch having a peripheral edge; and
at least one semi-rigid hoop extending continuously about and substantially surrounding a portion of the patch to urge the portion of the patch into a spread out configuration that is constructed and arranged to overlie the hernia, the hoop including opposing ends that are spaced apart to form an interruption adapted to be positioned at femoral vessels, the hoop having a resiliency that allows the hoop to deform from an initial shape and then return to the initial shape to return the portion of the patch to the spread out configuration.

11. The prosthesis according to claim 10, wherein the patch and the hoop are configured so that the patch maintains an amount of slack within the hoop allowing the patch to take a convex shape.

12. The prosthesis according to claim 10, further comprising at least one divider having first and second ends, the divider being positioned diametrically on the patch with the first and second ends joined to the hoop.

13. The prosthesis according to claim 12, wherein the divider has a curved shape to maintain the patch in a convex shape.

14. The prosthesis according to claim 10, further comprising first and second dividers, each of the first and second dividers having first and second ends, the first and second dividers being positioned diametrically on the patch and transverse to each other, the first and second ends of the first and second dividers being joined to the hoop.

15. The prosthesis according to claim 14, wherein the first and second dividers are positioned substantially perpendicular to each other.

16. The prosthesis according to claim 10, wherein the hoop includes at least one zone of less resistance proximate to at least one of the opposing ends adjacent the interruption, the zone of less resistance being adapted to enlarge the interruption.

17. The prosthesis according to claim 16, wherein the zone of less resistance permits the hoop to be broken to enlarge the interruption.

18. The prosthesis according to claim 10, wherein the patch has a slit adjacent at least one of the opposing ends of the hoop adjacent the interruption to form a tongue.

19. The prosthesis according to claim 18, wherein the tongue is substantially tension-free.

20. The prosthesis according to claim 18, wherein the tongue is adapted to be applied over the femoral veins.

21. The prosthesis according to claim 10, wherein the at least one hoop includes a first hoop and a second hoop that is concentric with and spaced inwardly from the first hoop.

22. The prosthesis according to claim 21, wherein the patch is free of material within the second hoop.

23. The prosthesis according to claim 21, further comprising at least one spoke interconnecting the first hoop and the second hoop.

24. The prosthesis according to claim 21, wherein the interruption is formed by a first interruption in the first hoop and a second interruption in the second hoop that is aligned with the first interruption.

25. The prosthesis according to claim 24, further comprising first and second spokes connecting opposing ends of the first hoop adjacent the first interruption with opposing ends of the second concentric hoop adjacent the second hoop interruption.

26. The prosthesis according to claim 25, wherein the patch is free of material between the first and second spokes.

27. The prosthesis according to claim 25, wherein the patch includes a tongue between the first and second spokes, the tongue adapted to be positioned over the femoral vessels.

28. The prosthesis according to claim 21, further comprising a thread that is threaded in the patch adjacent the first hoop.

29. The prosthesis according to claim 28, wherein the thread is adapted to form the prosthesis into a frustum having a lateral space by applying tension to ends of the thread.

30. The prosthesis according to claim 29, wherein the thread is removable from the patch to allow the patch to return to the initial shape.

31. A prosthesis for repairing a hernia, the prosthesis comprising:
a flexible patch having a peripheral edge;
a first semi-rigid element disposed along a portion of the patch, the first semi-rigid element having a first interruption; and
a second semi-rigid element disposed along a portion of the patch, concentric with and spaced inwardly from the first semi-rigid element, the second semi-rigid having a second interruption that is substantially aligned with the first interruption,
wherein the first and second semi-rigid elements have a resiliency to allow the first and second semi-rigid elements to deform from an initial shape and then return to the initial shape after being deformed to give the patch a memory of the initial shape.

32. The prosthesis according to claim 31, further comprising first and second spokes connecting opposing ends of the first semi-rigid element adjacent the first interruption with opposing ends of the second semi-rigid element adjacent the second interruption.

33. The prosthesis according to claim 32, wherein the patch is free of material between the first and second spokes.

34. The prosthesis according to claim 32, wherein the patch includes a tongue between the first and second spokes, the tongue adapted to be positioned over the femoral vessels.

35. The prosthesis according to claim 31, further comprising a thread that is threaded in the patch adjacent the first semi-rigid element.

36. The prosthesis according to claim 35, wherein the thread is adapted to form the prosthesis into a frustum having a lateral space by applying tension to ends of the thread.

37. The prosthesis according to claim 36, wherein the thread is removable from the patch to allow the patch to return to the initial shape.

* * * * *

UNITED STATES PATENT AND TRADEMARK OFFICE
CERTIFICATE OF CORRECTION

PATENT NO. : 6,669,735 B1
DATED : December 30, 2003
INVENTOR(S) : Pelissier

It is certified that error appears in the above-identified patent and that said Letters Patent is hereby corrected as shown below:

Title page,
Item [56], References Cited, U.S. PATENT DOCUMENTS, please add the following:

| | | |
|---|---|---|
| -- 2,671,444 | 03/1954 | Pease, Jr. |
| 3,463,158 | 08/1969 | Schmitt et al. |
| 3,739,773 | 06/1973 | Schmitt et al. |
| 3,875,937 | 04/1975 | Schmitt et al. |
| 4,561,434 | 12/1985 | Taylor |
| 4,693,720 | 09/1987 | Scharnberg et al. |
| 4,710,192 | 12/1987 | Liotta et al. |
| 4,796,603 | 01/1989 | Dahlke et al. |
| 4,865,026 | 09/1989 | Barrett |
| 5,116,357 | 05/1992 | Eberbach |
| 5,122,155 | 06/1992 | Eberbach |
| 5,141,515 | 08/1992 | Eberbach |
| 5,147,374 | 09/1992 | Fernandez |
| 5,254,133 | 10/1993 | Seid |
| 5,258,000 | 11/1993 | Gianturco |
| 5,290,217 | 03/1994 | Campos |
| 5,334,217 | 08/1994 | Das |
| 5,350,399 | 09/1994 | Erlebacher et al. |
| 5,366,460 | 11/1994 | Eberbach |
| 5,368,602 | 11/1994 | de la Torre |
| 5,433,996 | 07/1995 | Kranzler et al. |
| 5,456,720 | 10/1995 | Schultz et al. |
| 5,507,811 | 04/1996 | Koike et al. |
| 5,578,045 | 11/1996 | Das |
| 5,593,441 | 01/1997 | Lichtenstein et al. |
| 5,681,342 | 10/1997 | Benchetrit |
| 5,695,525 | 12/1997 | Mulhauser et al. |
| 5,697,978 | 12/1997 | Sgro |
| 5,702,416 | 12/1997 | Kieturakis et al. |
| 5,716,408 | 02/1998 | Eldridge et al. |
| 5,725,577 | 03/1998 | Saxon |
| 5,766,246 | 06/1998 | Mulhauser et al. |
| 5,769,864 | 06/1998 | Kugel |
| 5,824,082 | 10/1998 | Brown |
| 5,836,961 | 11/1998 | Kieturakis et al. |
| 5,876,447 | 03/1999 | Arnett |
| 5,916,225 | 06/1999 | Kugel |
| Des. 416,327 | 11/1999 | Kugel |
| 6,077,281 | 06/2000 | Das |
| 6,162,962 | 12/2000 | Hinsch et al. |
| 6,174,320 B1 | 01/2001 | Kugel et al. |
| 6,176,863 B1 | 01/2001 | Kugel et al. |
| 6,214,020 B1 | 04/2001 | Mulhauser et al. |
| 6,224,616 B1 | 05/2001 | Kugel |
| 6,267,772 B1 | 07/2001 | Mulhauser et al. |
| 6,280,453 B1 | 08/2001 | Kugel et al. |
| 2001/0027347 A1 | 10/2001 | Rousseau |
| 2001/0049539 A1 | 12/2001 | Rehil |
| 6,436,030 B2 | 08/2002 | Rehil |
| 2002/0147457 A1 | 10/2002 | Rousseau -- |

UNITED STATES PATENT AND TRADEMARK OFFICE
CERTIFICATE OF CORRECTION

PATENT NO. : 6,669,735 B1
DATED : December 30, 2003
INVENTOR(S) : Pelissier

It is certified that error appears in the above-identified patent and that said Letters Patent is hereby corrected as shown below:

<u>Title page, (cont.)</u>
FOREIGN PATENT DOCUMENTS, please add the following:

| | | | |
|---|---|---|---|
| -- EP | 0 827 724 | A2 | 03/1998 |
| FR | 2 719 993 | A1 | 11/1995 |
| FR | 2 735 353 | A1 | 12/1996 |
| FR | 2 778 554 | A1 | 11/1999 |
| WO | 92/06639 | A2 | 04/1992 |
| WO | 95/32687 | A1 | 12/1995 |
| WO | 96/09795 | A1 | 04/1996 |
| WO | 96/41588 | A1 | 12/1996 |
| WO | 97/22310 | A2 | 06/1997 |
| WO | 99/03422 | A1 | 01/1999 |
| WO | 99/20204 | A1 | 04/1999 |
| WO | 02/22047 | A1 | 03/2002 -- |

Signed and Sealed this

Twenty-second Day of June, 2004

JON W. DUDAS
*Acting Director of the United States Patent and Trademark Office*